United States Patent [19]

Toyoda et al.

[11] 4,181,489
[45] Jan. 1, 1980

[54] PROCESS FOR THE TREATMENT OF BYPRODUCTS OBTAINED IN THE PREPARATION OF PHTHALIC ANHYDRIDE

[75] Inventors: Yoshiaki Toyoda; Yoshiaki Teraji; Takaai Suzuki, all of Takaishi, Japan

[73] Assignee: Mitsui Toatsu Chemicals, Incorporated, Tokyo, Japan

[21] Appl. No.: 853,766

[22] Filed: Nov. 21, 1977

[30] Foreign Application Priority Data

Nov. 24, 1976 [JP] Japan ............................ 51/140186

[51] Int. Cl.² .......................................... F23D 11/44
[52] U.S. Cl. ................................. 431/11; 260/346.4; 260/346.7
[58] Field of Search ............... 203/31, 28, 29, 99, 203/14, 15; 260/346.7, 346.4; 431/285, 11

[56] References Cited

U.S. PATENT DOCUMENTS

| | | | |
|---|---|---|---|
| 1,993,886 | 3/1935 | Jaegier et al. | 260/346.7 |
| 2,786,805 | 3/1957 | Sullivan | 260/346.7 |
| 2,806,861 | 9/1957 | Cummings | 203/31 |
| 3,002,980 | 10/1961 | Michel | 260/346.7 |
| 3,041,251 | 6/1962 | Perfetti et al. | 203/31 |
| 3,280,009 | 10/1966 | Ackermann et al. | 260/346.7 |
| 3,834,855 | 9/1974 | Hummell | 431/11 |

*Primary Examiner*—Wilbur L. Bascomb, Jr.
*Attorney, Agent, or Firm*—Fisher, Christen & Sabol

[57] ABSTRACT

Byproducts obtained in the preparation of phthalic anhydride are treated by heating the byproducts to a temperature sufficient to maintain the byproducts in a molten state and thereafter atomizing the molten byproducts with atomizing air having a temperature of at least 60° C. for combustion. The byproducts may be low boiling point and/or high boiling point fractions obtained in the purification step by distillation of crude phthalic anhydride produced by the partial oxidation of ortho-xylene or naphthalene.

8 Claims, 1 Drawing Figure

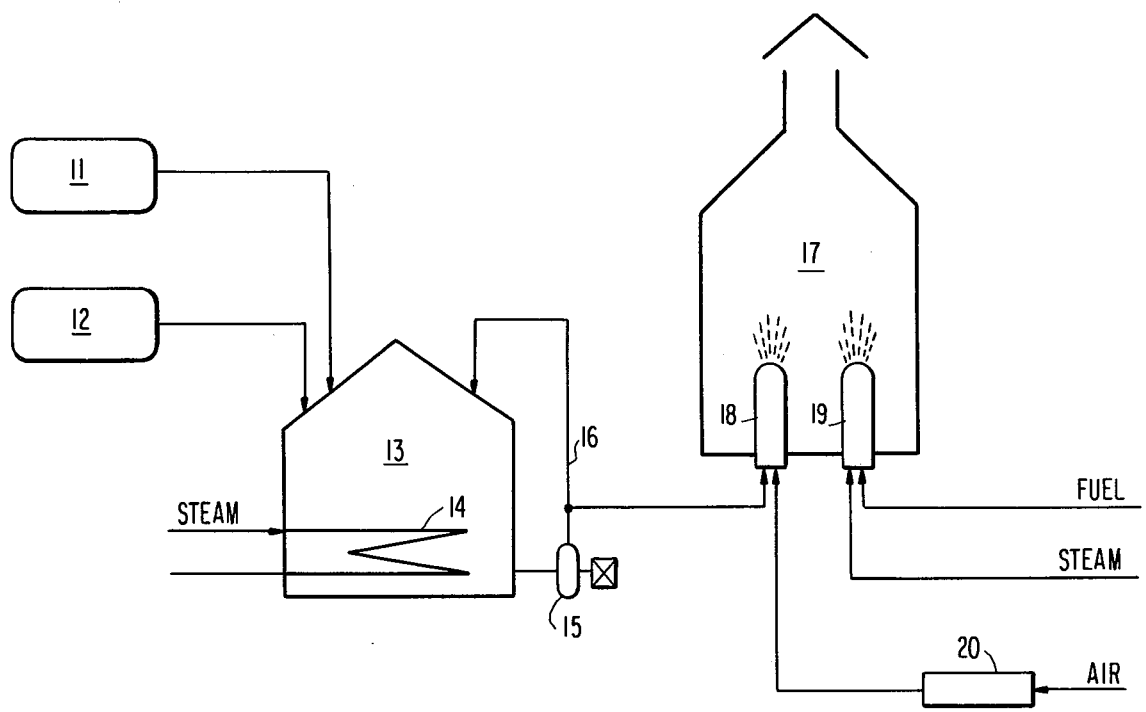

PROCESS FOR THE TREATMENT OF BYPRODUCTS OBTAINED IN THE PREPARATION OF PHTHALIC ANHYDRIDE

BACKGROUND OF THE INVENTION

1. Field of the Invention

This invention relates to a process for the treatment of byproducts produced during the preparation of phthalic anhydride, and more specifically of byproducts obtained in the purifying step by distillation of crude phthalic anhydride.

2. Description of the Prior Art

Phthalic anhydride is generally produced by the partial oxidation of ortho-xylene or naphthalene with air in the presence of a catalyst containing oxides of metals such as vanadium and titanium. The crude phthalic anhydride produced according to such processes normally contains a variety of impurities and, therefore, vacuum distillation is generally effected to remove low boiling point and high boiling point compounds contained in the crude phthalic anhydride. While the byproducts, i.e., thus separated low and high boiling fractions, contain valuable substances, the content of each of the substances is relatively small. For this reason, the separation and purification of such valuable substances from the byproducts require complicated procedures and increased costs and, thus, the recovery of such valuable substances has not been conducted hitherto.

Rather, the byproducts have been generally discharged into or allowed to be accumulated in proper places after being solidified by cooling. This is, of course, not desirable from the antipollution point of view. To solve this problem, one may consider treating the byproducts by combustion. However, since such byproducts are solid at normal temperature, handling thereof encounters a lot of difficulties. Moreover, because of their poor ignitibility and flammability, a combustion treatment is involved with a problem of accumulation of incombustible materials, which will create secondary environmental pollution.

SUMMARY OF THE INVENTION

It is an object of the present invention to provide a process which allows the treatment of byproducts obtained in the preparation of phthalic anhydride without creating secondary pollution.

It is another object of the invention to provide a process in which the byproducts are advantageously used as a heat source, e.g., as a part of a fuel for boilers.

It is a special object of the invention to provide a process which allows stable atomization of the byproducts and, thus, stable combustion thereof.

In accomplishing the foregoing objects, there has been provided according to the present invention a process for the treatment of byproducts obtained in the preparation of phthalic anhydride, which includes the steps of heating the byproducts to at least a temperature sufficient to maintain the byproducts in a molten state, and atomizing the molten byproducts, in a combustion zone, with atomizing air having a temperature of at least 60° C. for combustion.

The byproducts may be low and/or high boiling fractions obtained by the distillation of crude phthalic anhydride. The atomization is preferably conducted with the use of a dual fluid spray nozzle.

In a preferred aspect, 0.1 to 2 parts by weight of air of 60° to 290° C. are used for the atomization of one part by weight of the byproducts which are heated to at a temperature of 100° to 290° C. for maintaining desired molten state. Further, combustion air is additionally used for effecting the combustion of the atomized byproducts preferably in an amount of 7 to 25 parts by weight per one part by weight of the molten products.

In a preferred embodiment of the present invention, combustion of the byproducts is performed in combination with that of a fuel in a boiler and, for this purpose, a mono-fuel combustion burner for the byproducts is additionally attached to the boiler having a burner for the fuel.

DETAILED DESCRIPTION OF THE PREFERRED EMBODIMENT OF THE INVENTION

In the drawing:

The FIGURE is a schematic diagrammatic flow chart of the process of this invention. In the FIGURE, the numeral 11 is a low boiling point fraction-collection tower, numeral 12 is a high boiling point fraction-collection tower, numeral 13 is a storage tank, numeral 14 is a steam coil, numeral 15 is a pump, numeral 16 is a circulating pipe, numeral 17 is a combustion zone, numeral 18 is a dual fluid spray nozzle, numeral 19 is a fuel oil burner, and numeral 20 is an air heater.

The byproducts to be subjected to the treatment according to the process of the present invention are, generally, low and/or high boiling point fractions obtained in the distillation of crude phthalic anhydride produced by partial oxidation of orthoxylene or naphthalene. The low boiling fractions mainly contain phthalic anhydride, benzoic acid, maleic anhydride, o-tolualdehyde, while the high boiling point fractions include mainly phthalic anhydride, naphthoquinone, pyromellitic acid. These byproducts are solid at normal temperature and have low ignitibility and low flammability.

The byproducts are generally withdrawn from a low boiling point fraction-collecting tower and/or a high boiling point fraction-collecting tower, and are then introduced, either before or after being solidified, into a storage tank equipped with a suitable heating device such as a steam coil and/or an electric heater, where they are maintained at a temperature higher than their melting points, i.e., generally at a temperature of 100° to 290° C., preferably 120° to 250° C. In case the byproducts are composed of low boiling fractions alone, they are maintained at a temperature generally at least 100° C. preferably at least 120° C. in the storage tank. In the case of the byproducts containing high boiling fractions alone, they are generally heated to 120° to 290° C., preferably to 150° to 250° C.

The temperature of the molten byproducts is an important parameter to effect the combustion treatment of the byproducts completely. That is, in order to perform the complete combustion, liquid particles produced by the atomization of the byproducts must have sufficiently small particle sizes. For this reason, it is preferred that the temperature be so determined that the viscosity of the molten byproducts falls within the range of 10 to 90 centipores. The suitable temperature range is, however, dependent upon the kinds of the byproducts. For instance, when high boiling point fractions are employed as the byproducts, which have been obtained from crude phthalic anhydride produced from ortho-xylene, the temperature range is from 150° to 160°

C. to obtain the desired viscosity. In the case of high boiling fractions derived from naphthalene, the temperature is over 200° C. An ordinary skill could determine such suitable temperature range without much difficulty. When the byproducts are introduced into the storage tank in a solid state, they are able to be readily changed into a molten state by, for example, stirring with a stirrer provided in a storage tank or continuously withdrawing from and returning into the storage tank a portion of the molten byproducts by means of a circulating pump.

While either low boiling point fractions or high boiling fractions are able to be treated singly in accordance with the process of the present invention, it is preferred that both of these fractions be mixed together in the storage tank, so that high boiling fractions are more easily changed into molten state by being mixed with low boiling fractions which have a lower melting point, and the atomization of the byproducts is more easily conducted.

In the atomization of the byproducts in a combustion zone, a dual fluid spray nozzle is advantageously used, which may be a burner nozzle having two fluid passages, one passage being for a combustible fluid and the other for an atomizing gas. Examples of such burners are a spray burner, a steam or air jet type oil burner, a rotary burner, all of which are widely used in the art. A pressure jet type oil burner which is not included in a dual fluid nozzle type burner, cannot be used for the process of the present invention.

As the atomizing gas for effecting atomization of the molten byproducts, air is preferably used. In case steam is used as the atomizing gas, a burner nozzle is apt to be clogged with high boiling point blocking substances, such as orthophthalic acid, produced by hydration reaction of certain of the compounds contained in the byproducts, such as phthalic anhydride, with water produced by the condensation of steam at a time of initiation or during the stop of the combustion operation. Thus, careful check of the nozzle is required. In contrast, one encounters no such hydration problem in the case of air, thus ensuring very easy operations.

The atomizing air is heated to at least 60° C., preferably 60° to 290° C., by an air heater before it is supplied to a spray nozzle, so that it may serve to prevent the molten byproducts from being cooled. Lowering of the temperature of the molten byproducts is disadvantageous, because it causes an increase in the viscosity thereof or results in the solidification thereof. The increase in the viscosity may lead to enlargement of the particles size of atomized byproducts, which in turn results in lowering of ignitibility and flammability.

The amount of the pre-heated atomizing air may be determined from both the composition of the molten byproducts and the temperature of the atomizing air. Generally, 0.1 to 2 parts by weight of atomizing air are used per one part by weight of the molten byproducts.

In order to effect complete combustion of the byproducts, combustion air is additionally supplied to the combustion zone in an amount of 7 to 25 parts by weight, preferably 12 to 21 parts by weight, per one part by weight of the molten byproducts, by any suitable means.

As the combustion zone for effecting the combustion of the atomized molten byproducts, any type of incinerator may be employed such as an exclusive incinerator. However, because no problem of deterioration or corrosion of the incinerators is found to be involved in the combustion treatment of the byproducts according to the process of the present invention, it is not necessary to use such special exclusive incinerator. Rather, it is possible to continuously conduct a long period-treatment with the use of a conventional boiler using a fuel oil as fuel. For this purpose, a mono-fuel burner for the combustion of the byproducts may be additionally attached to the boiler to effect combustion of the fuel oil and the byproducts simultaneously in combination. In this case, the byproducts may be subjected to the combustion treatment in such an amount that corresponds to approximately up to 60 percent of the fuel oil based on the heat of combustion.

According to the process of the invention, the treatment of a waste produced as byproducts in the preparation of phthalic anhydride, which has become a difficult problem in the art, is able to be performed with the use of an inexpensive apparatus without creating secondary pollution, while making it possible to utilize the heat produced by the combustion treatment.

EXAMPLE 1

Molten byproducts produced in a system for preparing phthalic anhydride from ortho-xylene were successively withdrawn from a low boiling point fractions-collecting tower and a high boiling point fractions-collecting tower of a distillation apparatus, and were introduced into a storage tank equipped with a heating coil, where they were mixed by means of a pump provided outside of the tank for circulation and were maintained at 180° C. By means of a spiral pump, 61 Kg/h of the byproducts were pressurized and, after the removal of solids by a strainer, supplied, for atomization, to a steam or gas jet type oil burner having a dual fluid type nozzle for combustion of the byproducts, which was located in parallel to a fuel oil burner of a Dowtherm boiler furnace. Atomization of the molten byproducts was effected with 42 Kg/h of atomizing air having a temperature of 100° C. 184 Kg/h of a fuel oil were fed to the fuel oil burner for atomization with 67 Kg/h of atomizing steam. Ignition was effected by means of a pilot burner using propane gas as a fuel. The atomized byproducts were found to burn easily and completely. The combustion treatment was conducted continuously for one year. Inspection of the inside of the furnace revealed that almost no uncombusted materials were produced and accumulated therein.

The fact that 61 Kg/h of the byproducts was able to be treated, means that 35 Kg/h of the fuel oil could be saved to be consumed at the fuel oil burner of the boiler. Further, because no sulphur components is contained in the byproducts, the content of sulphur compounds in an exhaust gas discharged by the above-described combustion treatment in the boiler, is lower than that produced in a boiler using only the fuel oil as fuel.

EXAMPLE 2

Byproducts containing high boiling point fractions alone were subjected to a combustion treatment, without being mixed with low boiling point fractions, in the same manner and conditions as described in Example 1 hereinabove. The combustion treatment was conducted for one year while stopping and restarting the combustion operations once a month. No problem was observed to be involved in such stopping and restarting, and the combustion treatment was able to be performed satisfactorily similar to in Example 1. It was revealed that the consumption of the fuel oil was saved in an amount of 30 Kg/h.

Comparative Example 1

Combustion treatment was effected in the same manner and conditions as in Example 1 above, except that steam was substituted for the atomizing air. At first, steam heated to 130° C. and pressurized to the same level as the atomizing air in Example 1, was fed to the burner and, then, the molten byproducts were supplied to the burner. As a consequence, the tip of the burner was clogged with the byproducts.

The clogged burner was replaced with a new one, to which were fed the molten byproducts and atomizing steam simultaneously. Ignition and combustion were able to be suitably carried out. However, when such stopping and restarting test as described in Example 2 was conducted, the burner was found to be clogged at its tip upon restarting.

We claim:

1. A process for the treatment and combustion of byproducts containing some residual phthalic anhydride, obtained in the preparation of phthalic anhydride by the partial oxidation of orthoxylene or naphthalene which consists essentially of the steps of:
   (i) heating said byproducts containing some phthalic anhydride to a temperature sufficient to maintain the byproducts in a molten state;
   (ii) atomizing the molten byproducts in a combustion zone using atomizing air having a temperature of at least 60° C.; and
   (iii) combusting the atomized molten byproducts in the combustion zone with or without the addition of any additional air for combustion purposes, whereby complete combustion of the atomized molten byproducts is achieved, said phthalic anhydride in said byproducts not being removed therefrom at anytime during or between steps (i) to (iii).

2. The process as claimed in claim 1 wherein said atomizing step comprises introducing said molten byproducts and said atomizing air into a dual fluid spray nozzle of a burner provided in the combustion zone.

3. The process as claimed in claim 2 wherein said combustion is conducted in a boiler furnace in combination with a fuel supplied from a second burner of the furnace.

4. The process as claimed in claim 1 wherein said byproducts comprise low boiling point and/or high boiling point fractions obtained in the distillation of crude phthalic anhydride produced by the partial oxidation of orthoxylene or naphthalene.

5. The process as claimed in claim 1 wherein said heating step comprises heating said byproducts to a temperature of 100° to 290° C.

6. The process as claimed in claim 1 wherein said atomizing air has a temperature of 60° to 290° C.

7. The process as claimed in claim 1 wherein said combustion is effected with the use of combustion air in an amount of 7 to 25 parts by weight per one part by weight of the molten byproducts.

8. The process as claimed in claim 7 wherein said atomizing air is used in an amount of 0.1 to 2 parts by weight per one part by weight of said molten byproducts.

* * * * *